United States Patent [19]
Wise

[11] 3,970,431
[45] July 20, 1976

[54] CARBON MONOXIDE GAS DETECTOR

[75] Inventor: Henry Wise, Redwood City, Calif.

[73] Assignee: Stanford Research Institute, Menlo Park, Calif.

[22] Filed: Mar. 31, 1975

[21] Appl. No.: 563,481

Related U.S. Application Data

[63] Continuation-in-part of Ser. No. 435,631, Jan. 23, 1974, abandoned.

[52] U.S. Cl. .............................. 23/232 E; 23/254 E; 73/27 R; 148/6.3; 324/71 SN; 338/34; 340/237 R; 427/87; 427/108; 427/126
[51] Int. Cl.² ................. G01N 27/12; G01N 31/00
[58] Field of Search ........... 23/232 E, 254 E, 255 E; 73/23, 27 R; 324/71 SN; 338/13, 22 SD, 34; 340/237 R, 237 US; 29/620; 427/75 US

[56] References Cited
UNITED STATES PATENTS

| | | | |
|---|---|---|---|
| 2,020,305 | 11/1935 | Essig | 148/6.3 |
| 3,051,895 | 8/1962 | Carson | 324/71 SN |
| 3,547,835 | 12/1970 | Short | 338/22 SD X |
| 3,567,383 | 3/1971 | Langley et al. | 23/254 E X |
| 3,578,409 | 5/1971 | Silverman et al. | 23/254 E |
| 3,644,795 | 2/1972 | Taguchi | 338/34 X |
| 3,699,803 | 10/1972 | Sumi et al. | 73/27 R |
| 3,821,038 | 6/1974 | Schwuttke | 29/576 X |
| 3,865,550 | 2/1975 | Bott et al. | 23/232 E |

Primary Examiner—Joseph Scovronek
Attorney, Agent, or Firm—Lindenberg, Freilich, Wasserman, Rosen & Fernandez

[57] ABSTRACT

An indicator of the presence and changes in the carbon monoxide content of the air is provided by this invention. It operates by measuring the change in resistance of a silver oxide when exposed to carbon monoxide.

9 Claims, 3 Drawing Figures

CARBON MONOXIDE GAS DETECTOR

CROSS references TO RELATED APPLICATIONS

This application is a continuation-in-part of application Ser. No. 435,631, filed Jan. 23, 1974, entitled Carbon Monoxide Gas Detector, now abandoned.

BACKGROUND OF THE INVENTION

This invention relates to a new method and means for detecting the presence and changes in the concentration of carbon monoxide.

The need for a reliable, stable and simple device for measuring various levels of carbon monoxide exists. It can find use in areas such as mines, closed rooms and automobiles. Still another and very important use is as a fire detection device.

OBJECTS AND SUMMARY OF THE INVENTION

An object of this invention is to provide a device which can indicate the presence and amount of carbon monoxide, even though mixed with other gases.

Yet another object of this invention is the provision of a carbon monoxide indicating device which is reliable and long lived.

Still another object of the present invention is the provision of a novel and useful carbon monoxide monitor.

The foregoing and other objects of the invention are achieved by exposing a body of silver oxide to the atmosphere or to gases in which it is desired to detect carbon monoxide and measuring the change in conductivity that occurs. The body may be in the form of a pressed powder or granule pellet having a pair of spaced electrodes applied to the surface thereof or may be a thin film of silver oxide which is deposited over an insulating substrate on which there has been previously deposited a pair of spaced electrodes. It has been found that the conductivity of the silver oxide increases with an increase in the concentration of carbon monoxide to which the silver oxide is exposed, with a measurable change in conductivity beginning to be noted at 5 ppm of carbon monoxide in air and conductivity increasing in accordance with the increase in the concentration of the carbon monoxide. Also, the increase in conductivity changes more rapidly as there is an increase in the ambient temperature.

The electrodes are connected to any suitable indicator which responds to an increase in electrical conductivity of a material. This can be a volt meter, by way of example, or a relay which is energized by an increased current flow through the silver oxide body caused by an increase in the concentration of the carbon monoxide to which the film is exposed. When the relay is energized it may actuate an alarm.

The novel features of the invention are set forth with particularlity in the appended claims. The invention will best be understood from the following description when read in conjunction with the accompanying drawings.

DESCRIPTION OF THE PREFERRED EMBODIMENTS

In accordance with this invention, it has been found that a metal-oxide semi-conductor material, such as silver oxide, changes its electrical conductivity when it is exposed to changes in carbon monoxide concentrations which are greater than those usually found in the ambient. The usual concentration of carbon monoxide in air is one to two ppm. At those concentrations, the silver oxide remains stable and its conductivity remains stable. However, it was found that when the concentraion of the carbon monoxide in air, to which the silver oxide is exposed, becomes greater tha 5 ppm, its conductivity begins to change and as the concentration of the carbon monoxide gets greater and greater its conductivity increases therewith. The speed or rate of response of this invention is quite rapid. For exaple, it responds to changes in CO concentrations at a rate between 1 to 10 percent per second at CO levels between 100 and 800 ppm.

By way of a explanation of the theory involved, but not to be construed as a limitation on the invention, it is believed that oxygen, which is adsorbed on the silver oxide surface, is removed by carbon monoxide resulting in changes in space charge regions in the silver oxide. This reaction is reversible, in air at relatively low concentrations of carbon monoxide, typically 30 ppm, or less, for example. However, at high concentrations of carbon monoxide a reaction with lattice oxygen occurs which is irreversible.

It should be further noted that the rate of response to changes in carbon monoxide level has been found to be greatly accelerated by raising the temperature of the detector and by the addition of foreign metal oxides.

Figure 1:
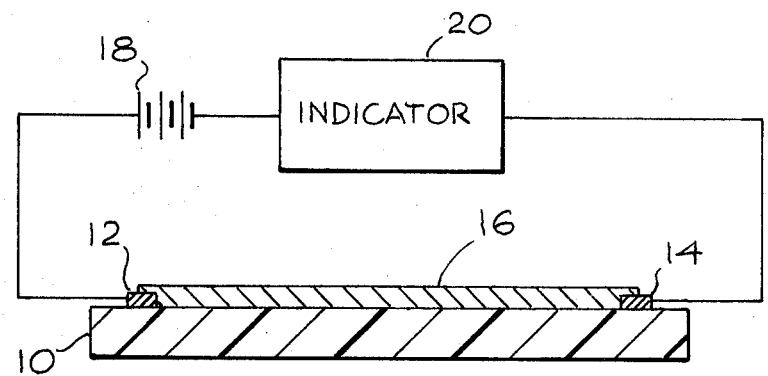
FIG. 1 is a schematic drawing of an embodiment of the invention.

Referring now to FIG. 1, there may be seen a cross-sectional view of an illustrative embodiment of the invention. Upon a substrate 10, which can be an insulator such as silica, there is deposited a pair of spaced contacts, respectively 12, 14, which are made of an inert metal which will not interact with silver, such as gold. Over these contacts and over the surface of the substrate there is evaporated a thin film, 16, of silver. The film is oxidized to a thickness of 1,000 to 10,000 angstroms by exposure to atomic oxygen using such means as an electrodeless oxygen discharge, or exposure to an oxygen rich hydrogen flame, or by exposure to ozone which is being thermally decomposed, or by electrochemical anodic oxidation.

The contacts 12, 14 are connected to a source of potential 18 in series with an indicator 20. The indicator may be one of these previously recited or may be an ammeter which indicates the amount of current as well as any changes in current as the conductivity of the silver oxide changes. The amount of current, or voltage shown by an indicator may be calibrated to indicate both the quantity of CO present as well as the rate of change in concentration thereof. The indicator or sensor may take the form of a relay which when actuated, actuates an alarm device, or any other suitable indicator which is responsive to a change in current flow (or voltage) as the conductivity of the silver oxide coating changes with exposure to carbon monoxide.

Figure 3:
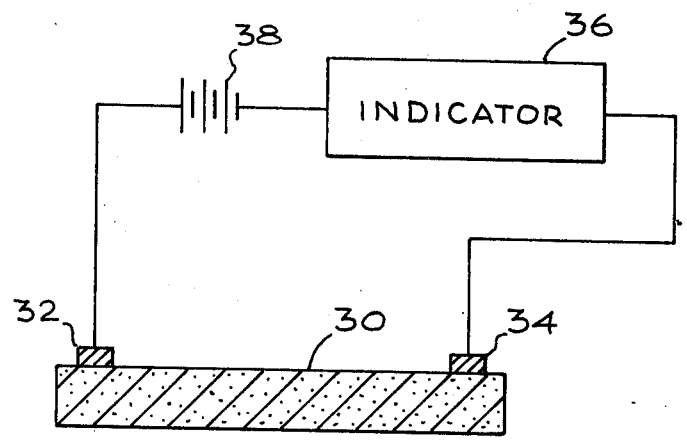
FIG. 3 is a schematic drawing of another embodiment of the invention.

Another, and preferred form, which the invention may take is shown in FIG. 3 which shows in cross section a pressed silver oxide 30 pellet to which inert electrodes respectively 32, 34 are attached. A conductance indicator 36, is connected in series with a battery 38 between these electrodes in tests conducted with a specimen in the form of a pressed cylinder of granular silver having a dimension of 0.5 inches in diameter and 0.05 inches in height, an electrical conductivity on the order of $10^{-6}$ (ohm-cm)$^{-1}$ was measured. With voltages applied between 0.1 to 1 volt, currents between $10^{-7}$ and $10^{-6}$ amps were measured in air in the absence of cabon monoxide. The response time of the device to a change in the carbon monoxide level was found to have been greatly accelerated by raising the temperature of the semi-conductor. The temperatue of 100°C was used and the relative rate of change of conductivity was found to be 15% per second at a carbon monoxide level of 100 ppm.

By way of illustration, and not to be considered as a limitation upon the invention, a procedure for making the silver nitrate pellet comprises dissolving, for example, one-half pound of $AgNO_3$ in 200 ml of distilled water. Heat may be used to hasten solution.

Prepare a solution of 75 gm anhydrous $Na_2CO_3$ in 800 ml of distilled water.

At room temperature add the $Na_2CO_3$ solution to the $AgNO_3$ solution while stirring with a glass rod. A curdy, yellow precipitate $Ag_2CO_3$ will form. After the two solutions are completely mixed there will be a 5 gm excess of a liquid. This liquid and the $Ag_2CO_3$ precipitate are poured through a large Bushner funnel on a suction flask, using a No. 1 grade filter paper. The mixture should be poured in such a way as to form a cake covering the bottom of the funnel evenly. The cake should be kept moist to prevent cracking.

The cake is then washed with 12 successive 500 ml portions of distilled water, keeping the cake moist but adding each successive portion only after the preceding one has just about completely passed through the cake. Allow the cake to such dry and then transfer the cake, in the form of large lumps to a large evaporating dish and place in an oven at 225°C for 12 to 16 hours. This prolonged heating causes complete decomposition of the $AgCO_3$.

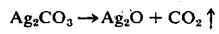

$$Ag_2CO_3 \rightarrow Ag_2O + CO_2 \uparrow$$

Any lumps are broken down by crushing or milling to granular size. Then, after screening, granules in the range between 10 to 40 microns (in diameter) are selected and placed in a die having a desired pellet shape and size. There a pressure on the order of 3,000 lbs/sq. in. is applied to form the pellet.

Electrodes may be applied to the pellet by evaporating or painting gold contacts at desired locations thereon. Alternatively, the required electrical contact may be established by fastening metal leads to desired locations directly on the pellet by any suitable clamping means or spring loaded device. A silver oxide pellet is activated for use as a CO detector by heating it, in air, at a temperature on the order of 275°C between 5 and 10 minutes. This seems to remove some of the remaining water vapor and other foreign gases and prepare the surfaces of the pellet granules for adsorption of oxygen. It is the removal of this surface adsorbed oxygen by the cabon monoxide to which the pellet is exposed that increases the conductivity of the pellet at low carbon monoxide concentrations.

Figure 2:
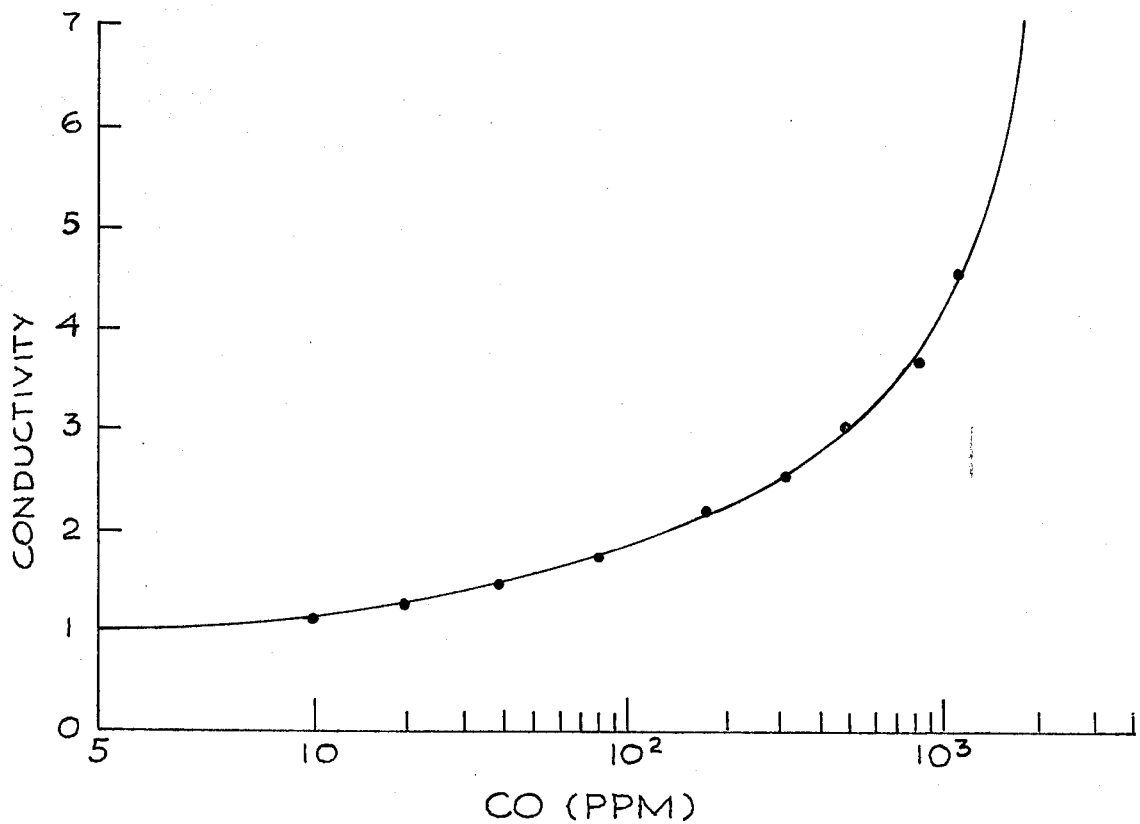
FIG. 2 is a curve showing the response characteristics of an embodiment of the invention to various concentrations of carbon monoxide in air.

FIG. 2 shows a curve of relative conductivity vs. CO concentration changes, illustrative of the response characteristics of an embodiment of this invention at various concentration of carbon monoxide in air, with the air temperature being on the order of 115°C. The large change in conductivity and its rapid rise with the increase in concentrations of carbon monoxide should be readily apparent from this curve. Since a smouldering fire generates from 20 to 100 ppm and a fire may generate as much as 1000 ppm of carbon monoxide in air, the value of this invention as a fire detector should be readily apparent. The silver oxide surface is stable in air and the conversion of the silver oxide to metal silver due to reaction with carbon monoxide is irreversible, i.e., metallic silver so produced is not reoxidized in air. However, in view of the sensitivity exhibited of a device constructed in accordance with this invention, its utility as a sensor for the presence of increasing, undesirable concentrations of carbon monoxide is also quite apparent.

While the invention has been described as taking the form of a film or pellet of granular silver, it is to be understood that it can take other forms, such as that of a single crystal of silver oxide. These forms are generically referred to herein as a body.

It is known that the introduction of an additive of a high valence metal oxide into silver oxide increases the oxidizing power of the silver oxide. Illustrative of such dopants are high valence metal oxides such as cobaltic oxide ($Co_2O_3$), 0.2% of which can be mixed with silver oxide, or manganese oxide ($MnO_2$), 0.1% to 0.5% of which can be mixed with silver oxides. The introduction of these additives has the effect, when used with this invention, of increasing the rate of change of the resistance of the silver oxide with changes in the concentration of the carbon monoxide to which the silver oxide body is exposed. Such additives may be introduced by mechanical admixtue of finely ground powder or by conventional aqeuous solution techniques.

There has accordingly been shown and described herein a novel, useful and relatively inexpensive detector for carbon monoxide as well as a new use for silver oxide as a detector of carbon monoxide.

What is claimed:

1. A method of measuring the presence and the amount of carbon monoxide present in gases comprising exposing a body consisting of silver oxide to said gases, and measuring the change of electrical conductivity of said body of silver oxide in response to carbon monoxide in said gases.

2. A method as recited in claim 1 wherein said body consisting of silver oxide is a pellet of compressed silver oxide granules.

3. A method as recited in claim 1 wherein said body consisting of silver oxide is a film of silver oxide deposited on a substrate.

4. A method of measuring the presence and the amount of cabon monoxide present in gases comprising immersing a body consisting of silver oxide in gases containing carbon monoxide, applying a voltage across a predetermined part of said silver oxide body, measuring the change in current flowing across said predetermined part of said silver oxide body caused by the carbon monoxide present in said gases, and displaying said change of current flowing as an indication of the amount of cabon monoxide present.

5. The method as recited in claim 4 wherein said body consists of a compressed pellet of silver oxide granules.

6. The method as recited in claim 4 wherein said body consists of a film of silver oxide deposited on a substrate.

7. The method as recited in claim 4 wherein said body consisting of silver oxide is doped with a high valence metal oxide selected from a group consisting of manganese oxide and cobaltic oxide.

8. A method of measuring the presence and amount of carbon monoxide present in gases comprising
heating a pellet consisting of of silver oxide granules for from 5 to 10 minutes in the atmosphere at a temperature on the order of 275°C,
cooling said pellet to the ambient temperature,
immersing said pellet in said gases, and
measuring the change of electrical conductivity of said pellet caused by the carbon monoxide in said gases.

9. A method of measuring the presence and amount of carbon monoxide present in gases comprising
exposing a pellet of compressed granules consisting of silver oxide doped with a high valence metal oxide selected from a group consisting of manganese oxide and cobaltic oxide, and
measuring the change of electrical conductivity of said pellet in response to carbon monoxide in said gases.

* * * * *